United States Patent
Schuhmacher et al.

(10) Patent No.: US 7,754,496 B2
(45) Date of Patent: Jul. 13, 2010

(54) DETERMINATION OF FREE FRACTIONS

(75) Inventors: Joachim Schuhmacher, Wuppertal (DE); Christian Kohlsdorfer, Wuppertal (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 1020 days.

(21) Appl. No.: 10/567,056

(22) PCT Filed: Aug. 4, 2004

(86) PCT No.: PCT/EP2004/008708
§ 371 (c)(1), (2), (4) Date: Jun. 26, 2006

(87) PCT Pub. No.: WO2005/017528
PCT Pub. Date: Feb. 24, 2005

(65) Prior Publication Data
US 2007/0111208 A1 May 17, 2007

(30) Foreign Application Priority Data
Aug. 16, 2003 (EP) .................................. 03018512

(51) Int. Cl.
G01N 33/543 (2006.01)
G01N 33/537 (2006.01)

(52) U.S. Cl. ...................... 436/518; 436/524; 436/526; 436/527; 436/538

(58) Field of Classification Search ................. 436/518, 436/524, 526, 527, 538
See application file for complete search history.

(56) References Cited

U.S. PATENT DOCUMENTS

| 5,411,730 A | * | 5/1995 | Kirpotin et al. | .......... 424/9.322 |
| 5,801,064 A | * | 9/1998 | Foresman et al. | ........... 436/518 |
| 6,977,305 B2 | * | 12/2005 | Leung et al. | ................ 548/450 |

FOREIGN PATENT DOCUMENTS

WO   WO 03/010330 A2   2/2003

OTHER PUBLICATIONS

Austin, R. P., et al., "The Influence of Nonspecific Microsomal Binding on Apparent Intrinsic Clearance, and its Prediction from Physicochemical Properties", Drug Metabolism and Disposition, 30(12): 1497-1503 (2002).

Boyd, B. J., et al., "Using the Polymer Partitioning Method to Probe the Thermodynamic Activity of Poorly Water-Soluble Drugs Solubilized in Model Lipid Digestion Products", J. Pharm. Sci., 92(6): 1262-1271 (Jun. 2003).

(Continued)

*Primary Examiner*—Jacob Cheu
*Assistant Examiner*—Pensee T Do
(74) *Attorney, Agent, or Firm*—Edwards Angell Palmer & Dodge LLP; Ralph A. Loren; Weiying Yang

(57) ABSTRACT

The invention relates to methods for the determination of pharmacological properties of substances, such as, e.g., chemical substances. The invention also relates to methods and kits for use in the determination of the free fraction, $f_u$, of pharmacologically active compounds in aqueous solutions and serum. The invention also relates to the above methods in which solid particles, coated with a lipophilic medium, are used.

8 Claims, 1 Drawing Sheet

OTHER PUBLICATIONS

Loidl-Stahlhofen, A., et al., "Multilamellar Liposomes and Solid-Supported Lipid Membranes (TRANSIL): Screening of Lipid-Water Partitioning toward a High-Throughput Scale", Pharm. Res., 18(12): 1782-1788 (2001).

Loidl-Stahlhofen, A., et al., "Solid-Supported Lipid Membranes as a Tool for Determination of Membrane Affinity: High-Throughput Screening of a Physicochemical Parameter", J. Pharm. Sci., 90(5): 599-606 (2001).

Santos, N. C., et al., "Quantifying molecular partition into model systems of biomembranes: an emphasis on optical spectroscopic methods", Biochimica et Biophysica Acta, 1612: 123-135 (2003).

Schuhmacher, J., et al., "Determination of the Free Fraction and Relative Free Fraction of Drugs Strongly Bound to Plasma Proteins", J. Pharm. Sci., 89(8): 1008-1021 (Aug. 2000).

Schmitz, A. A. P., et al., "Interactions of Myristoylated Alanine-Rich C Kinase Substrate (MARCKS)-Related Protein with a Novel Solid-Supported Lipid Membrane System (TRANSIL)", Analytical Biochem., 268: 343-353 (1999).

Poulin, P., et al., "Prediction of Pharmacokinetics Prior to In Vivo Studies. 1. Mechanism-Based Prediction of Volume of Distribution", J. Pharm. Sci., 91(1): 129-156 (Jan. 2002).

Veronese, M. E., et al., "Plasma Protein Binding of Amiodarone in a Patient Population: Measurement by Erythrocyte Partitioning and a Novel Glass-Binding Method", Br. J. Clin. Pharmac., 26: 721-731 (1988).

* cited by examiner

DETERMINATION OF FREE FRACTIONS

TECHNICAL FIELD

The invention relates to methods for the determination of pharmacological properties of substances, such as, e.g., chemical substances. The invention also relates to methods and kits for use in the determination of the free fraction, $f_u$ of pharmacologically active compounds in aqueous solutions and serum. The invention also relates to the above methods in which solid particles, coated with a lipophilic medium, are used.

BACKGROUND

Quantification of protein binding of new chemical entities is an important early screening step during drug discovery and is of fundamental interest for the estimation of safety margins during drug development.

Commonly used methods for the determination of protein binding, e.g. ultrafiltration or equilibrium dialysis are readily adaptable to high throughput but in the case of lipophilic drugs, being strongly bound to plasma proteins, their use is limited due to unspecific adsorption. Due to the fact that in recent years a trend to more lipophilic drugs is observed[4], the need for new techniques that overcome these problems and that can be adapted to high throughput is increasing.

One technique that was especially designed for the determination of protein binding of lipophilic drugs is based on the distribution of drugs between plasma and erythrocytes or buffer and erythrocytes, respectively[5]. In the following, this technique is referred to as the partitioning method. Unfortunately, precision of the basic method is poor in the case of highly protein bound drugs (i.e., in the case of drugs which show high affinity to proteins).

A modification of the partitioning method is known to the person skilled in the art[6], which overcomes that disadvantage by determining $f_u$ at several dilutions of plasma via linear regression. Another modification of the partition method circumvents the most critical step in the determination of $f_u$ via partitioning, the handling of the drug in protein free medium[7].

It is known that Transil® is a widely used substance for the high throughput determination of membrane affinities in drug discovery[9,10]. A person skilled in the art will recognise that Transil® comprises solid silica particles that are coated with egg yolk phosphatidylcholine.

Recently a new approach for the determination of relative free fractions by equilibrium dialysis was reported using plasma of different species in each dialysis chamber[16]. However, validation of this approach is still outstanding. Own experiments using this method for drugs highly bound to plasma proteins ($f_u$<0.5%) did not yield valid results (data not shown).

The closest prior art discloses a modification of the partitioning method that uses diluted plasma from various species but only erythrocytes from a single species[8], thereby circumventing the necessity to isolate fresh erythrocytes for each individual test organism being under investigation in cross-species studies.

The new method is an advancement of the previously described erythrocytes partitioning technique[8]. The most time-consuming step in this method is the preparation of the erythrocytes: they are obtained by centrifugation of fresh, heparinised blood and have to be washed three times in isotonic phosphate buffer. Furthermore, the washing of the erythrocytes has to be done very carefully to avoid hemolysis. However, in some cases hemolysis can not be completely prevented and erroneous results due to binding of drugs to hemoglobin can not be excluded. All these difficulties are avoided using solid-supported lipid membranes. The material is commercially available and was especially developed to determine membrane affinities in HTS format (as an alternative to liposomes)[9,10].

DESCRIPTION OF THE INVENTION

From the above mentioned state the technical problem to be solved by the current invention is to provide a new and improved method for the determination of the free fraction, $f_u$, of substances, such method being amenable to a high-throughput experimental approach.

This problem is solved by providing a new method which is a major improvement of the previously mentioned erythrocytes partition method[8]. It is based on the distribution of drugs between plasma water, plasma proteins and solid-supported lipid membranes (e.g., Transil®). Substituting the erythrocytes by solid-supported lipid membranes (e.g., Transil®) simplifies the execution of protein binding studies by partitioning dramatically, and it makes it particularly suitable for high throughput experiments. Because of the increased specific weight of the support material, phase separation is easily achieved with Transil®. This is a major advantage over the use of liposomes or RP-18 material used in, e.g., HPLC column packings.

As mentioned above, it is known that Transil® is a widely used substance for the determination of membrane affinities in drug discovery[9,10]. The determination of membrane affinities, however, is very different from the determination of the free fraction.

The finding that erythrocytes can be substituted by solid-supported lipid membranes is a very surprising one in view of the fact that erythrocytes are rather complex structures, actually being living cells, having a lipid bi-layer membrane which is host to a wide variety of functional enzymes, ion channels, receptors and the like.

It is furthermore known to a person skilled in the art that ionisation of the silica bead surface tends to have an effect on the binding properties of such particle[10]. The fact that the unavoidable ionisation of the solid support does not negatively affect determination of the free fraction is an unforeseen and unexpected finding.

Furthermore, the fact that the distribution of the compound between Transil® and the buffer is not affected by the presence of plasma constituents is also unforeseen. This, however, is a prerequisite for the application of Transil® in methods of the invention.

For reasons stated above, it cannot be deemed obvious that measurements performed with solid supported membranes, such as, e.g., Transil® beads can be taken as a surrogate measurement for the far more sumptuous experiments using freshly isolated erythrocytes.

For validation purposes, compounds covering a wide range of lipophilicities (logP=1.9 to 5.6) and large differences in free fractions (0.02% to~35%) were selected. The validation results show excellent agreement in $f_u$ as determined by the method of the current invention, by the partitioning method (using erythrocytes as "stationary phase"), and by ultrafiltration. Free fractions could be exactly determined with differences between the various methods below 20% even in the case of $f_u$ values below 0.1%. Species differences in $f_u$ in the case of Drug I, Drug II and Drug IV of Table 2 were almost identical regardless of whether being determined by the Transil® method or by a classical partitioning method using erythrocytes. Thus, the results show that the erythrocytes can be replaced by solid-supported lipid membranes. Moreover, the new method is applicable to determine very low ($f_u<0.1\%$) and very high free fractions ($f_u>5\%$), giving rise to a much wider range of application than currently available methods. Since precision and accuracy are comparable regardless of very low or high free fractions, the method proves to be especially suited for lipophilic drugs strongly bound to plasma proteins. For lipophilic drugs the investigation of the free fraction by commonly methods like ultrafiltration or equilibrium dialysis is limited since lipophilic drugs often show non-specific adsorption to the ultrafiltration device or to the dialysis membrane.

It has to be noted that the most critical step in the case of lipophilic drugs (that tend to adsorb to surfaces) is the determination of the partition coefficient in buffer. However, as described below adsorption to glass material can be avoided by accepting an accumulation of critical drugs in the lipid phase. Although the precision of the method may decrease if partitioning is far away from equal distribution accuracy increases since systematic errors are avoided. In such cases the demands on the validation of the analytical assay for low concentrations increase. On the other hand results as obtained by that procedure are much more reliable than those obtained by e.g. ultrafiltration or equilibrium dialysis, because with these methods results may be biased due to adsorption to the ultrafiltration device or the dialysis membrane. The comparable free fractions as obtained in the case of Drug II of Table 2 either using this procedure or conventional methods, prove this approach yields reliable results.

In conclusion, the methods of the invention produce valid results both with radioactivity measurement and with methods that are more common in drug discovery, like LC-MS/MS. The method is applicable to determine a wide range of membrane affinities and free fractions but is especially suited for the examination of free fractions of drugs strongly bound to plasma proteins. The method can be easily adapted to high throughput and is therefore suited for the determination of protein binding during drug discovery as well as for the execution of extended protein binding studies during drug development. Finally, by using Transil® for both the determination of membrane affinity and protein binding of a drug the most important input parameters for physiologically based modeling can be examined simultaneously.

A "suspension" within the meaning of the invention, is any mixture comprising solid particles and a liquid.

Transil® particles are to be understood as being one example for particles, having suitable characteristics. Other particles, having the such suitable characteristics, can readily be applied in methods of this invention.

The invention relates to:
1. A method for the determination of the free fraction of a substance comprising
   (a) incubation of the substance with a suspension of particles, other than erythrocytes, having a lipophilic surface, in a substantially protein-free aqueous medium, for the determination of the distribution of the substance between the particles and said substantially protein free medium;
   (b) incubation of the substance with a suspension of particles, other than erythrocytes, having a lipophilic surface, in a protein-containing aqueous medium, for the determination of the distribution of the substance between the particles and said protein-containing aqueous medium; and
   (c) determination of the free fraction of the substance from the distributions determined under (a) and (b).

2. A method of count 1, wherein said suspension of particles is selected from a group of suspensions comprising
   (a) a suspension of particles having a solid core;
   (b) a suspension of particles having a solid core comprising a silica bead; and
   (c) a suspension of Transil® particles.
3. A method of count 1 or 2, wherein the protein-containing aqueous medium is plasma.
4. A method of any of counts 1 to 3, wherein the substantially protein-free aqueous medium is a buffer solution.
5. A method of any of counts 1 to 4, wherein said incubations of said substance with said suspensions of particles is on a plate having multiple cavities or on a 96-well-plate.
6. A method of any of counts 1 to 5, wherein the solid core is a ferromagnetic solid core.
7. A method for the determination of the relative free fraction of a substance in a first species in relation to the free fraction of the same substance in a second species comprising
   (a) determining the membrane affinity in plasma ($MA_{plasma}$) of said substance for said first species,
   (b) determining the membrane affinity in plasma ($MA_{plasma}$) of said substance for said second species,
   (c) determining the relative free fraction from the results determined under steps (a) and (b).
8. A kit for use in any of the methods of counts 1 to 7, comprising a plate having multiple cavities, a buffer solution, plasma, and particles selected from a group of particles comprising
   (a) particles having a solid core;
   (b) particles having a solid core which is a silica bead; and
   (c) Transil® particles.
9. The kit of count 8, comprising plasma of two different species.
10. A kit of count 8 or 9, wherein specific amounts of particles are placed within said cavities of said plate.

EXAMPLES

Drugs and Reagents

Figure 1:
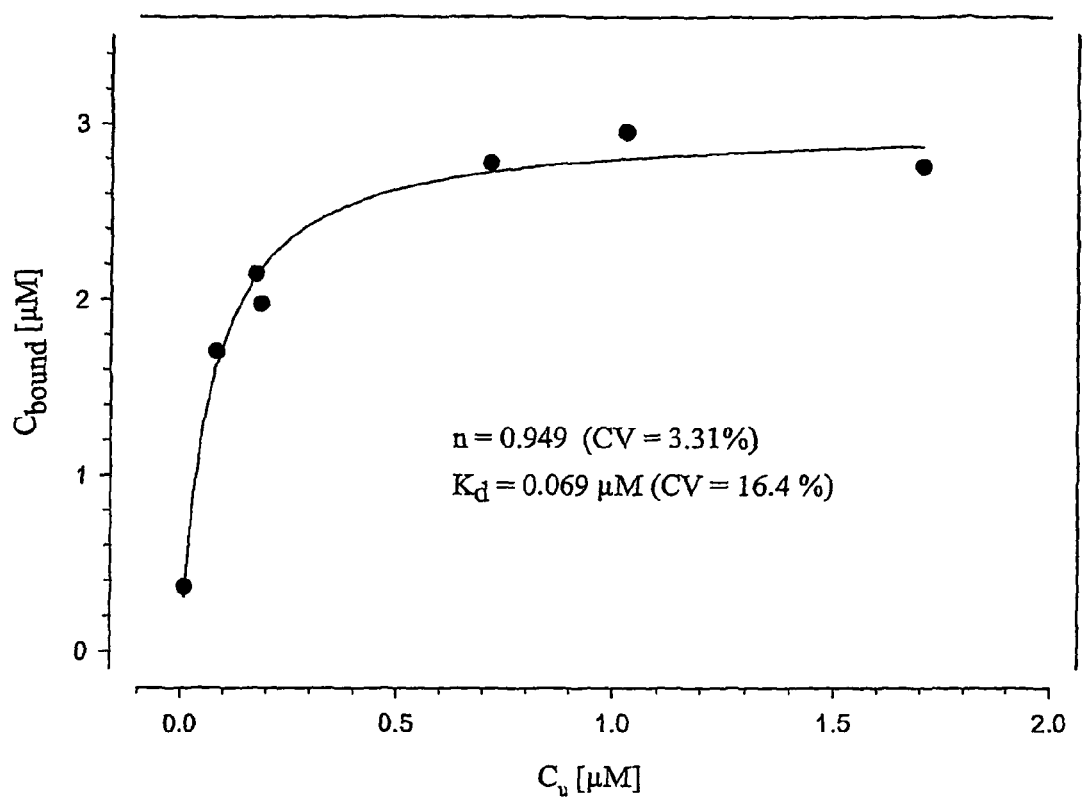
FIG. 1
Drug I of Table 2: Determination of binding parameters in human $\alpha_1$-acid glycoprotein (AGP) upon incubation with increasing drug concentrations in a 3.15 µM AGP solution. Data were fitted to the equation: $C_{bound}=n \cdot C_{AGP} \cdot C_u/(K_d+C_u)$ using Sigma Plot 2.01 ($C_{bound}$=bound drug concentration, n=number of binding sites, $C_{AGP}$=AGP concentration in the assay, $C_u$=unbound drug concentration, $K_d$=dissociation constant).

Both unlabeled (drugs I to V) and $^{14}$C-labeled drugs (VI and VII) as well as reference compounds for analytics were synthesised in the chemistry department of Bayer AG. Solvents used were of HPLC grade. All other chemicals were of analytical grade.

Transil® (silica bead coated with egg yolk phosphatidylcholine) was purchased from NIMBUS Biotechnologie GmbH, Leipzig, Germany. This material comprises porous silica beads, covered with a unilamellar liposomal membrane, non-ovalently bound to the bead. The solid supported lipid membranes are suspended in 20 mM sodium phosphate buffer (pH 7.4). The lipid content as well as the dry weight of the respective batch are provided by the supplier. The lipid content of the respective batches used in our experiments was between about 10 and 65 µl/ml suspension. For determinations in HTS format, 96-well plates with removable glass inserts (0.5 or 1.5 ml) were used.

Biological Material

Mouse plasma from male CD1 mice (Hsd/Win:CD1), rat plasma from male Wistar rats (Hsd/Win:Wu), dog plasma from female Beagle dogs, monkey plasma from female Rhesus monkeys was used. Human plasma was obtained from healthy Caucasian volunteers. Pooled plasma of at least 3 individuals was obtained after centrifugation of freshly heparinised blood samples and stored at ≦−20° C. until usage.

Stability

The stability of the test substances in plasma of different species was tested prior to protein binding studies.

Determination of Unlabeled Drugs

The determination of drugs I to V in plasma was done after precipitation of proteins with acetonitrile. Measurement of drug IV in plasma was performed by HPLC analysis using the same equipment and under similar chromatographic conditions as described earlier[8]. All other unlabeled drugs were analyzed by LC/MS-MS on an API 3000 (MDS Sciex, Ontario Canada) triple quadrupole tandem mass spectrometer operated in positive ion multiple reaction monitoring mode (MRM) using similar procedures described elsewhere[11]. A 2300 HTLC system (Cohesive Technologies, Franklin, Mass.) was used as HPLC system and operated in the laminar flow mode. Chromatography was performed using gradient elution. A CTC HTC PAL autosampler (CTC Analytics AG, Zingen, Switzerland) was used.

Measurement of Radioactivity

The radioactivity concentrations were determined by standard procedures as described earlier[12].

Protein Binding by Classical Methods

Ultrafiltration, equilibrium dialysis and the determination of the free fraction of a drug via distribution between erythrocytes and plasma were performed as previously described[8,12].

Example 1

Determination of Protein Binding Via Distribution Between Diluted Plasma and Transil®

Protein binding of all drugs was determined via partitioning between diluted plasma and Transil® in vitro. All incubations were performed in glass tubes. An isotonic potassium phosphate buffer, pH 7.4 (Dulbeccos PBS, Sigma D8534) was used for diluting the plasma.

The total incubation volume was generally between 0.3 and 1 ml. The diluted plasma (150 to 980 µl) of the test species was pipetted into glass tubes and Transil® (10 to 300 µl) was added. The test substance dissolved in a small volume of a suitable solvent was added to the Transil®-plasma suspensions.

The degree of the dilution and the Transil®-volume should be chosen with respect to the expected $f_u$ value. For strongly bound compounds a higher dilution/and or higher Transil®-volumes must be considered (see below).

The Transil®-plasma suspensions were incubated at room temperature on a laboratory shaker for 30 minutes. After incubation, Transil® was separated from the aqueous phase by centrifugation at 1800 g for 10 min, after taking aliquots of 50 to 100 µl for determining the actual concentrations in the Transil®-plasma suspensions.

The radioactivity concentration in the suspension was determined directly after incubation. The radioactivity concentration (or the drug concentration in the case of HPLC or LC/MS-MS analytics) in plasma was determined after centrifugation.

The determination of the Transil®/buffer partitioning (which is a measure for membrane affinity, MA) was performed in the same manner. In the case of high lipid/buffer concentration ratios ($MA_{buffer}$ values>20000) the Transil®-suspensions were diluted with isotonic phosphate buffer, pH 7.4 (up to 20 fold) to avoid pipetting of volumes below 10 µl.

Example 2

Estimation of $MA_{buffer}$ and $f_u$ in Human Plasma

An estimate of the membrane affinity was calculated by a QSAR approach as described in Stahlhofen et al.[10]. The free fractions in plasma were estimated using a proprietary software developed at Bayer AG. (Alternatively, other approaches to obtain first estimates for MA and $f_u$ may be used, e.g. log $D_{7.4}$ for estimation of membrane affinities of neutral compounds and estimates of $f_u$ based on experimental data for drugs from the same compound class).

Calculation of $f_u$

The free fraction in diluted plasma was calculated as the ratio of the partition coefficients for the Transil®/plasma' ($MA_{plasma}$) and the Transil®/buffer distribution ($MA_{buffer}$).

The calculation of $MA_{buffer}$ was performed as follows: The total amount of drug in the assay ($n_{total}$) was obtained using the total concentration in the Transil®-buffer suspension and the respective incubation volume ($V_{total}$) the concentration in the buffer ($C_{buffer}$) and the volume of the silica beads ($V_{silica}$) as well as the lipid volume ($V_{lipid}$) according to:

1)
$$MA_{buffer} = \frac{C_{lipid}}{C_{buffer}} = \frac{n_{total} - C_{buffer} \cdot (V_{total} - V_{silica} - V_{lipid})}{V_{lipid} \cdot C_{buffer}}$$

where the volume of the silica beads was obtained from the dry weight of the respective Transil® batch ($dw_{Transil®}$) the volume of the Transil®-suspension added ($V_{Transil®}$) the dilution factor of Transil® ($dil_{Transil®}$) the lipid volume ($V_{lipid}$) the density of silicagel ($\rho_{silica}$=2.1 g/ml) and the density of the lipids ($\rho_{lipid}$=1 g/ml) according to equation 2). The dry weight as well as the lipid content (k) of the respective Transil® batches were given by the supplier in the certificate of analysis.

2)
$$V_{silica} = \frac{dw_{Transil®} \cdot V_{Transil®} \cdot dil_{Transil®} - V_{lipid} \cdot \rho_{lipid}}{\rho_{silica}}$$

The lipid volume in the assay was calculated from the lipid content of the respective Transil® batch and the volume and the dilution factor of the Transil®-suspension added:

$$V_{lipid} = k \cdot V_{Transil®} \cdot dil_{Transil®}$$

In a second experiment, the total amount in the Transil®-plasma suspension and the concentration in diluted plasma, $C_{plasma}'$, were determined. The partitioning between Transil® and the diluted plasma (the apparent membrane affinity in diluted plasma), $MA_{plasma}'$, was calculated as:

4)
$$MA_{plasma}' = \frac{n_{total} - C_{plasma}' \cdot (V_{total} - V_{silica} - V_{lipid})}{V_{lipid} \cdot C_{plasma}'}$$

The free fraction in diluted plasma ($f_u'$) was calculated as the ratio of the two partition coefficients:

5)
$$f_u' = \frac{MA_{plasma}'}{MA_{buffer}}$$

The free fraction in undiluted plasma was then calculated from the $f_u$-values in diluted plasma and the dilution factor a, as described earlier[1] (e.g. a=0.1 in the case of 10-fold diluted plasma). It has to be noted that $f_u'$ should be below about 50% to avoid a higher variability in the back-calculated free fraction in native plasma[8].

6)
$$f_u = \frac{a \cdot f_u'}{1 - f_u' \cdot (1-a)}$$

Example 3

Calculation of Optimal Transil® Volumes for New Compounds

Equations 1-3 can be rearranged to calculate the optimal Transil® volume for the determination of MA for a new compound. The calculated $MA_{buffer}$ values and free fractions are used as initial estimates for the calculation. Optimal assay conditions are fulfilled if the amounts of drug at equilibrium in the lipid phase and in buffer (or plasma) are equal ($n_{buffer}'$ or $n_{plasma}' = n_{lipid} = 0.5 \cdot n_{total}$) (Stahlhofen et al.[10]). Thus the expression ($n_{total}/n_{lipid} - 1$) in the subsequent equation equals 1 and the optimal $V_{Transil®}$ for Transil®/buffer partitioning can be calculated as:

7)
$$V_{Transil®} = \frac{V_{total} \cdot \varrho_{silica}}{\left( \begin{array}{c} MA_{buffer} \cdot k \cdot (n_{total}/n_{lipid} - 1) \cdot \varrho_{silica} + \\ dw_{Transil®} + k \cdot (\varrho_{silica} - \varrho_{lipid}) \end{array} \right) \cdot dil_{Transil®}}$$

The calculation for Transil®/plasma partitioning is similar to that of the Transil®/buffer partitioning, only the value for $MA_{buffer}$ has to be substituted by $MA_{plasma}'$ whereas it holds true:

8)
$$MA_{plasma}' = f_u' \cdot MA_{buffer} = \frac{f_u}{a + f_u \cdot (1-a)} \cdot MA_{buffer}$$

with a being the dilution factor of plasma, e.g. a=0.1 in the case of 10-fold diluted plasma[8].

Example 4

Concentration Dependence of MA

Distribution is only independent from drug concentration if the amount of lipid is much greater than the amount of drug in the lipid phase: lipid content/$n_{lipid} \geq 100$ [Mol/Mol].

The ratio lipid content/$n_{lipid}$ is calculated according to:

9)
$$\text{Lipid content}/n_{lipid} = \frac{V_{lipid} \cdot \varrho_{lipid}/MW_{lipid}}{n_{total} \cdot (n_{lipid}/n_{total})/MW_{drug}}$$

By rearrangement of the above equation the maximum drug concentration that can be used in an incubation ($C_{total,max}$) can be calculated (under the assumption that lipid content/$n_{lipid}$=100):

10)
$$C_{total,max} = \frac{V_{lipid} \cdot \varrho_{lipid}/MW_{lipid}}{V_{total} \cdot (n_{lipid}/n_{total})/MW_{drug} \cdot 100}$$

The buffer- or plasma concentration at equilibrium is calculated from the actually added concentration ($C_{total}$) as follows:

11)
$$C_{plasma}' = \frac{C_{total} \cdot V_{total} \cdot (1 - n_{lipid}/n_{total})}{V_{total} - (V_{silica} + V_{lipid})}$$

The plasma concentration as related to native plasma is then calculated from the plasma concentration in diluted plasma and the dilution factor a (e.g. a=0.1 in the case of 10-fold diluted plasma).

11a)
$$C_{plasma} = \frac{C_{plasma}'}{a}$$

Example 5

Comparison of Free Fractions Obtained with the Transil® Method Versus Free Fractions Determined with Other Techniques For validation purposes drugs with a wide range of physicochemical properties and free fractions were selected. LogP (pH 7.5) values were calculated to be 3.6, 5.6, 1.9, 2.5, 2.6, 2.6 and 2.1 for drugs I to VII, respectively. Free fractions of the validation compounds were determined either by distribution of the drugs between diluted plasma and Transil® or by the distribution method as described earlier. In the case of drug V, protein binding was examined by ultrafiltration as reference method. Partitioning between buffer and Transil® was determined at a single drug concentration, typically at 200 µg/l. Usually comparisons were performed using the same batch of plasma to avoid differences in protein binding because of batch to batch variability.

A complete data set with typical values for the Transil®-volumes, the dilution factor of plasma, the drug concentrations in the suspension and in plasma at equilibrium is given in Table 1.

Table 2 summarises the results obtained with non-radiolabelled drugs in plasma from different species at a total concentration of about 200 µg/l. The free fraction of drug I amounted to 0.81% and 0.20% in rat and human plasma as determined by the Transil® method. These values are close to the ones determined with the erythrocytes partitioning method ($f_u$=0.91 and 0.24%, respectively). For the highly lipophilic drug II, very low, but similar free fractions were determined in mouse, monkey and human plasma (~0.050%). The free fraction in rat plasma was somewhat higher (~0.80%). The $f_u$ values as determined by the erythrocytes partitioning method were almost identical. In the case of drug III comparison of free fractions were only performed in rat plasma: $f_u$ amounted to 1.62% and 1.49% as determined by partitioning between plasma and Transil® or plasma and erythrocytes. About a 5 fold difference in free fractions (human/rat) was observed for drug IV. The free fractions were determined to be 4.41 or 1.09% in rat and human plasma, respectively, by distribution between plasma and Transil®. The corresponding values as determined by partitioning between plasma and erythrocytes were 4.97 and 0.96%, respectively. As a last example drug V, a compound with a very high free fraction in human plasma was chosen. In that case the reference value for $f_u$ was obtained by ultrafiltration: the free fraction amounted to 39.5 and 33.3% in human plasma as determined by distribution between plasma and Transil® or by ultrafiltration, respectively.

In Table 3 a summary of results as obtained for two $^{14}$C-labeled drugs is given. Free fractions were determined at 3 different drug concentrations (n=3/concentration) on 2 or 3 different days. Experiments using Transil®-or the erythrocyte distribution method were performed in parallel. There were no differences in free fractions in the concentration range tested and the results as obtained on different days were almost identical. Therefore, mean values and standard deviations are listed. In the case of drug VI very similar free fractions were determined in rat and human plasma: $f_u$ amounted to about 0.02% as determined by partitioning between diluted plasma and Transil®. The respective values as obtained with the erythrocytes partitioning technique were about 0.025 and 0.020% in rat and human plasma, respectively. In mouse plasma the free fraction amounted to about 0.087% as determined with both methods. The free fraction in dog plasma amounted to about 0.041 or 0.034% as determined by the new method or by the erythrocytes partitioning technique.

The free fraction of drug VII as examined in mouse, rat, dog and human plasma using the Transil® method amounted to 2.07, 3.59, 2.07 and 1.11%, respectively. The corresponding values using the erythrocytes partitioning technique were comparable (with slightly higher values for human plasma): $f_u$ amounted to 2.60, 3.77, 2.12 and 1.71% in mouse, rat, dog and human plasma, respectively. In the case of dog plasma variability of the results was somewhat higher than usual (coefficient of variation 14-31%) since plasma of different dogs was used to investigate inter day variability.

Example 6

Incubation in 96 Well Plates

The assay can easily be adapted to high-throughput format as demonstrated by Loidl-Stahlhofen et al.[9,10] for the determination of $MA_{buffer}$ values. To avoid adsorption of lipophilic drugs, 96 well plates with glass inserts should be used for all incubations. Furthermore, the actual concentrations in Transil®-buffer suspensions are determined to monitor adsorption. Results can only be accepted if the concentration deviation is below 20% of the theoretical concentration.

In silico values for $MA_{buffer}$ and $f_u$ can be used to tune the experimental conditions ($V_{Transil®}$ and plasma dilution factor) for optimum precision. Since these in silico values may have a high degree of uncertainty it is suggested to perform incubations at 2 different Transil®-volumes so that at least one incubation is carried out under acceptable $n_{buffer}/n_{lipid}$ conditions (see below) even if the MA estimate differs considerably from the true value. Furthermore it is recommended to determine $MA_{buffer}$ values at first, since the experiments with plasma then can be designed more exactly. Neglecting $V_{silica}$ and $V_{lipid}$ in comparison to $V_{total}$ leads to a simplified version of equation 7:

12)
$$V_{Transil®} = \frac{V_{total}}{MA_{buffer} \cdot k \cdot dil_{Transil®} \cdot (n_{buffer}/n_{lipid})}$$

with

13)
$$\frac{n_{buffer}}{n_{lipid}} = \frac{n_{buffer}}{n_{total} - n_{buffer}} = \frac{n_{total}}{n_{lipid}} - 1$$

The theoretical optimum for $V_{Transil®}$ is calculated from equation 12 with $n_{buffer}/n_{lipid}$=1. In case the true $MA_{buffer}$ is 5 fold higher than the estimated value used for the calculation of $V_{Transil®}$, $n_{buffer}/n_{lipid}$ is approximately 0.2. As can be seen from equation 13, such a case would not have a relevant effect on the precision of the MA determination because $n_{buffer}$ is directly determined via $C_{buffer}$ and $n_{total}$ is much bigger than $n_{buffer}$. In the other case of the $MA_{buffer}$ being 5 fold lower than the estimated value, $n_{buffer}/n_{lipid}$ is about 5, leading to a small difference between $n_{total}$ and $n_{buffer}$ in the denominator of equation 13. Thus a considerable decrease in precision is the consequence. Therefore, it is recommended to perform the $MA_{buffer}$ determination at an additional $V_{Transil®}$ which is about 5 fold higher than the calculated value for equal distribution between buffer and the lipid phase. It is suggested to have not more than 70% of the total amount in the buffer phase, leading to an upper limit of $n_{buffer}/n_{lipid}$ of about 2.3.

Similarly, the optimum $V_{Transil®}$ for the determination of $MA_{plasma}'$ is calculated based on the expected $f_u$, the measured $MA_{buffer}$ and the plasma dilution factor for plasma. $MA_{buffer}$ in equation 12 is substituted by $MA_{plasma}'$ as described in equation 8. As can be seen from equation 8 an under—or overestimation results in an almost proportional under- or overestimation of $MA_{plasma}'$ in the case of free fractions below 10%. Therefore, the same considerations with respect to precision as outlined above for $MA_{buffer}$ are also valid for $f_u$. As a consequence, the use of an additional, about 5 fold higher $V_{Transil®}$ is also recommended for the determination of $MA_{plasma}'$. Alternatively, the dilution factor for plasma can be 5 fold increased or an appropriate combination of plasma dilution and Transil®-volume is chosen.

An example is given in Table 4 for a hypothetical drug with a free fraction of 0.50% and a $MA_{buffer}$ of 10000. Accepting a $n_{buffer}/n_{lipid}$ of 2.3 a $MA_{buffer}$ range with the 2 Transil®-volumes calculated from 865 to above 100000 is covered. For the determination of $MA_{plasma}'$ the Transil®-volume is kept constant but the dilution factor is 5 fold increased resulting in a $f_u$ range covered from 0.041 to 5.0%. It has to be taken into account that the free fraction in the diluted plasma should be below about 50% to avoid a higher variability in the back-calculated values[8]. This condition limits the upper value of $f_u$ that can be determined (see Table 4). Therefore, it is recommended to calculate the maximum dilution factor for plasma at first by rearranging equation 6 according to:

14)
$$a = \frac{f_u \cdot (1 - f_u')}{f_u' \cdot (1 - f_u)}$$

For the calculation of the dilution factor the upper value of $f_u$ (e.g. 10 fold higher as the calculated free fraction) is used, as done in the example shown in Table 4. This results in a dilution factor of about 0.02. This value is now used for the for the calculation of the optimal Transil®-volume for a free fraction of 0.5%.

These examples show that with the procedure described above $MA_{buffer}$ values and free fractions can be determined in high throughput format even if the true- and estimated values differ by a factor of 10 in both directions.

Example 7

Determination of Concentration Dependence of the Free Fraction

Typically incubations in buffer or (diluted) plasma are performed at a concentration of 200 µg/l to ensure that the ratio Lipid content/$n_{lipid}$ (see equation 9) is above 100 and the concentration at equilibrium as related to native plasma, is at least 10 fold lower than the molar concentration of the main binding protein in plasma. This procedure is usually sufficient during drug discovery. However, during drug development the free fraction has to be determined additionally at much higher concentrations as observed e.g. in toxicokinetic experiments. The maximum concentration that can be used in incubation under the pre-condition that the ratio Lipid content/$n_{lipid}$ is at least 100, is calculated using equation 10. The plasma concentration at equilibrium as related to native plasma is then calculated according to equation 11 and 11a under consideration of the dilution factor of plasma. Table 5 gives an example for 2 hypothetical drugs with free fractions of 0.10% and 0.50%, respectively. The $MA_{buffer}$ values are assumed to be 50000 and 10000, respectively. As can be seen, the concentration as related to native plasma can be increased by increasing the dilution of plasma: using undiluted plasma in the incubation a maximum concentration at equilibrium of 263 µM can be reached, whereas a much higher concentration (393 µM) is obtained using 100 fold diluted plasma. The influence of dilution is not so pronounced in the case of drug B: equilibrium concentration as related to native plasma in increased from 263 to 289 µM. These examples demonstrate that free fractions can be determined at very high plasma concentrations by properly adjusting the dilution factor of plasma. However, the influence of the dilution factor may be small for some combinations of $MA_{buffer}$ and free fraction (see example B).

For drug I concentration dependence of $f_u$ to human $\alpha_1$-acid glycoprotein (AGP) was investigated and binding parameters (number of binding sites, n, and the dissociation constant, $K_d$) were calculated (see FIG. 1). The $K_d$ was estimated to be 0.069 µM and n was close to 1, indicating that AGP is a major binding protein in human plasma (assuming that the APG concentration in human plasma is 16 µM the free fraction as calculated from n and $K_d$ amounts to about 0.43%, the measured $f_n$ being 0.20 to 0.24%, see Table. 2). This example shows that the method as described herein correctly assesses dose dependence of $f_u$ and is appropriate for the determination of binding parameters.

Example 8

Determination of $MA_{buffer}$ in Cases of Very Lipophilic Drugs

Although all incubations are performed in test tubes of glass, in some cases adsorption can not be avoided in incubations where the drugs are handled in protein free solutions. This is detected in a huge deviation of added and measured concentration in the reference. For a few drugs, e.g. drug II even the use of silanised or siliconised tubes did not lead to a significant improvement and only 20 to 50% of the added concentrations were found in the reference. To minimise adsorption the following procedure has turned out to be very useful: usually Transil®-volumes are adjusted to give a 1:1 distribution of the drug between the lipid phase and buffer as described in materials and methods. Accepting $n_{buffer}/n_{lipid}$ ratios much smaller than 1 (e.g. 0.1 or 0.05) leads to higher Transil®-volumes as calculated by equation 12. As lined out above, a small $n_{buffer}/n_{lipid}$ ratio still allows a precise determination of MA, however, the requirements for the assay precision at low concentrations increases. The use of higher Transil®-volumes has a strong impact on the maximal drug concentration ($C_{total,max}$) that can be used for incubation according to equation 10 but without effecting buffer concentration at equilibrium (equation 11). An example is given in Table 6 for 2 drugs with membrane affinities of 10 000 and 10 0000, respectively: under normal incubation conditions ($n_{buffer}/n_{lipid}=1$) $C_{total,max}$ is only about 1.2 and 0.12 µg/ml. About 5.5 fold higher concentrations can be used accepting a $n_{buffer}/n_{lipid}$ ratio of 0.1 that can be further increased by about 2 fold at an $n_{buffer}/n_{lipid}$ ratio of 0.05. The use of such high drug concentrations has the advantage that reactive sites on the glass tubes are saturated and that adsorption is avoided due to the strong accumulation in the lipid phase. With that procedure we were able to completely avoid adsorption even for critical drugs and to determine reliable results. The comparison of free fractions for drug II as determined by the Transil® method or by the erythrocytes partitioning technique shows excellent agreement (see Table 2).

Example 9

Determination of Relative $f_u$ Between Different Species

In many cases it is more relevant to know relative free fractions between different species than the absolute values (e.g. exposure in humans and exposure of animals in safety studies). Relative $f_u$ can be calculated without determining $MA_{buffer}$ as follows:

15)
$$f_{u,rel} = \frac{f_{u,1}}{f_{u,2}} = \frac{MA_{plasma,1}}{MA_{plasma,2}}$$

with $f_{u,1}$ and $f_{u,2}$ being the free fractions in species 1 and 2 and $MA_{plasma,1}$ and $MA_{plasma,2}$ the respective lipid/plasma partition coefficients. In cases where it is necessary to determine plasma/lipid distribution in diluted plasma (for strongly bound drugs) a very close approximation of the true $f_{u,rel}$ can be obtained by:

16)
$$f_{u,rel} \approx \frac{a_1 \cdot MA_{plasma,1}}{a_2 \cdot MA_{plasma,2}}$$

with $a_1$ and $a_2$ being the dilution factors for plasma from species 1 and 2, respectively.

Considerations concerning accuracy and precision of this procedure have been performed for the erythrocytes partitioning method as described earlier[8].

Example 10

Determination of the Free Fractions in Hts Format

The following procedure is in place in our labs to determine free fractions in HTS format: Membrane affinities in buffer are determined first at two different Transil®-volumes using calculated $MA_{buffer}$ values to plan the experiments as described above. This approach assures that membrane affinities can with certainty be determined in one experiment with good precision, even if the calculated and measured affinities strongly differ. Measured membrane affinities in buffer are then utilised to design the experiments in diluted plasma of the species of interest. Once again incubations with plasma are performed at two different Transil®-volumes and/or at different plasma dilutions in order to cover a wide range of possible free fractions in one experiment.

Example 11

Determination of the Free Fraction with Non-linear Protein Binding

The Transil® method also correctly indicates a non-linearity in protein binding as demonstrated for the concentration dependent binding of drug I in solutions of $\alpha_1$ glycoprotein. Binding parameters could be determined with good precision. Concentration dependence of $f_u$ in plasma at relevant concentrations as observed e.g. in toxicokinetic experiments can be performed up to very high drug concentrations since the distribution of drugs to the lipid membranes is not dependent on drug concentration provided the amount of lipids is much greater than the amount of drug in the lipid phase. The maximum concentration in native plasma (under consideration of the dilution factor of plasma) that can be reached without disturbing distribution to the lipids, depends on the membrane affinity and the free fraction of the respective drug.

As shown above, it can be increased by adjusting the dilution factor of plasma. It has to be noted that for the assessment of the concentration dependence of $f_u$, the Transil®-volumes may be adjusted according to the $f_u$ expected to work under optimal assay conditions ($n_{buffer}/n_{lipid} \sim 1$). As a general guide protein binding is considered to be independent from concentration unless an at least 10 fold excess of free binding proteins is given. Assuming a 1:1 binding to the protein for drugs strongly bound to plasma proteins ($f_u < 2\%$), a 2-fold increase in $f_u$ is expected at a drug concentration reaching 50% of the concentration of the main binding protein. At a drug concentration reaching 75% of the protein concentration an about 4-fold increase of $f_u$ is expected (see Appendix 1). In the event of significant binding of a drug to different plasma proteins a comparable increase of free fractions occurs at higher drug concentrations depending on the concentrations of the respective binding proteins and the affinity constants of the drug to the proteins.

Example 12

Determination of the pH Dependency of the Free Fraction

As reported by Loidl-Stahlhofen et al.[10], the solid supported lipid membranes are stable up to high pH values. Therefore pH dependence of free fraction, as necessary during drug development, can also be monitored.

Example 13

Estimation of the Increase of $F_U$ in Dependence of Drug Concentration in Plasma assuming binding to a single Protein The binding of a drug to a protein can be described as follows:

A1)
$$C - C_u = \frac{n \cdot C_{Prot} \cdot C_u}{K_d + C_u}$$

where C is the total drug concentration, $C_u$ the unbound drug concentration, $C_{Prot}$ is the total concentration of protein, n is number of binding sites on the protein and $K_d$ is the dissociation constant of the protein substance-complex. Introducing $C_u = C \cdot f_u$ and rearrangement yields:

A2)
$$C = \frac{n \cdot C_{Prot} \cdot f_u + K_d \cdot (f_u - 1)}{f_u - f_u^2}$$

In the case of a low free fraction the term $(f_u - f_u^2)$ approaches f, and the expression $K_d \cdot (f_u - 1)$ approaches $-K_d$, therefore equation A2) simplifies to:.

A3)
$$C = n \cdot C_{Prot} - \frac{K_d}{f_u}$$

The drug concentration ($C_x$) at which an x-fold increase of $f_u$ is observed is then:

A4)
$$C_x = n \cdot C_{Prot} - \frac{K_d}{x \cdot f_u}$$

Assuming at least a tenfold excess of free binding sites on the protein, $K_d/f_u$ equals $n \cdot C_{Prot}/(1-f_u) \sim n \cdot C_{Prot}$ in cases of small free fractions, the percentage of drug concentration to the protein concentration can be expressed as:

A5)
$$\frac{C_x}{n \cdot C_{Prot}} = \left(1 - \frac{1}{x}\right) \cdot 100\%$$

e.g. a 2 fold increase in the free fraction is observed if the drug concentration is 50% of the protein concentration. Or, an x-fold increase of free fraction is observed at:

A6)
$$x = \frac{n \cdot C_{Prot}}{n \cdot C_{Prot} - C_x}$$

The error in equations A5 and A6 is only below about 10% if $f_u$ in the solution containing higher drug concentrations is below 8%.

The following abbreviations were used in the above:

| | |
|---|---|
| C | Total drug concentration in a solution of a protein |
| $C_u$ | Unbound drug concentration in a solution of a protein |
| $C_{Prot}$ | Total protein concentration in plasma |
| $f_u$ | Fraction of free (unbound) drug in a solution of a protein |
| $K_d$ | Dissociation constant of the protein drug-complex |
| n | Number of binding sites on the protein |
| $C_x$ | Total drug concentration in a solution of a protein at which an x-fold increase of free fraction is observed |

TABLE 1

A complete data set with typical values for the Transil ®-volumnes, the dilution factor of plasma, the drug concentration in the suspension and in plasma at equilibrium is shown. Unbound fractions ($f_u$) of Drug I in rat and human plasma, determined by partitioning between diluted plasma of the corresponding species and Transil ®. Plasma and buffer concentrations were measured by LC/MS-MS. Arithmetic means of 4-5 determinations and standard deviations (in parentheses) are given (the lipid content used of the batches Transil ® was 9.1 and 12.5 µl/ml for rats and man, respectively, the dry weight was 223 and 207 mg/ml, respectively).

| Species | $V_{total}$ [ml] | $V_{Transil}$ [µl] | n | Dilution of Plasma | $C_{total}$ [µg/l] | $C_P$ [µg/l] | $C_{Lipid}$ [mg/l] | $MA_{plasma}$ | $f_u$ diluted Plasma [%] | $f_u$ undiluted Plasma [%] |
|---|---|---|---|---|---|---|---|---|---|---|
| Wistar rat, male | 0.5 | 100 | 5 | 1:5 | 117 (4.49) | 74.8 (3.00) | 24.0 (2.58) | 322 (41.8) | 4.87 (0.632) | 0.812 (0.110) |
| human male | 0.5 | 100 | 5 | 1:30 | 111 (10.9) | 51.5 (2.56) | 24.1 (3.65) | 468 (58.4) | 7.07 (0.883) | 0.203 (0.0272) |

A mean $MA_{buffer}$ ratio of 6611 (584), was used for calculation of $f_u$-values (n = 8)

TABLE 2

Comparison of unbound fractions ($f_u$) of validation drugs in plasma of various species as determined either by partitioning between diluted plasma of the corresponding species and Transil ® (A) or by classical methods (B = erythrocyte plasma partitioning, C = ultrafiltration)[a]

| | Drug I $f_u$ (%) | | Drug II $f_u$ (%) | | Drug III $f_u$ (%) | | Drug IV $f_u$ (%) | | Drug V $f_u$ (%) | |
|---|---|---|---|---|---|---|---|---|---|---|
| Method | A | B | A | B | A | B | A | B | A | C |
| CD1 Mouse, male | | | 0.0484 (0.00694) | 0.0461 (0.00741) | | | | | | |
| Wistar rat, male | 0.812 (0.110) | 0.913 (0.0684) | 0.0795 (0.00841) | 0.0864 (0.0085) | 1.62 (0.159) | 1.49 (0.298) | 4.41 (0.259) | 4.97 (0.435) | | |
| Rhes.monk., male | | | 0.0535 (0.00451) | 0.0516 (0.00745) | | | | | | |
| human male | 0.203 (0.0272) | 0.238 (0.0432) | 0.0507 (0.0105) | 0.0478 (0.00669) | | | 1.09 (0.166) | 0.961 (0.113) | 39.5 (3.18) | 33.3 (1.37) |

[a]Plasma concentrations were measured by LC/MS-MS or by HPLC.
Arithmetic means of 5-10 determinations and standard deviations (in parentheses) are given Mean $MA_{buffer}$ ratios: 15-6119: 6611 (584), 59-1762: 547263 (64268), 59-7939: 816 (46.2), 60-4409: 10368 (1523), 71-9678: 534 (n = 5-13)

TABLE 3

Comparison of unbound fractions ($f_u$) of validation drugs in plasma of various species as determined either by partitioning between diluted plasma of the corresponding species and Transil ® (A) or by erythrocyte plasma partitioning (B)[a]

| Method | Drug VI Concentration range[b] (mg/l) | Drug VI $f_u$ (%) A | Drug VI $f_u$ (%) B | Drug VII Concentration range[b] (mg/l) | Drug VII $f_u$ (%) A | Drug VII $f_u$ (%) B |
|---|---|---|---|---|---|---|
| CD1 mouse female | 0.231-24.0 | 0.0872 (0.0122) | 0.0868 (0.0102) | 0.023-3.59 | 2.07 (0.30) | 2.60 (0.08) |
| Wistar rat, male | 1.00-39.2 | 0.0193 (0.0035) | 0.0253 (0.0040) | 0.014-3.33 | 3.59 (0.40) | 3.77 (0.30) |
| Beagle dog female | 0.474-35.2 | 0.0414 (0.0129) | 0.0340 (0.0047) | 0.023-3.36 | 2.07 (0.41) | 2.12 (0.55) |
| human male | 1.17-38.8 | 0.0195 (0.0008) | 0.0200 (0.0021) | 0.024-3.82 | 1.11 (0.06) | 1.71 (0.13) |

[a]Plasma concentrations were measured by radio-analytics of the $^{14}$C-labeled compounds.
Determinations were performed at three different drug concentrations (n = 3/concentration) on three different days in the case of rat plasma or on 2 different days in the case of dog and human plasma, respectively.
Arithmetic means of 18-27 determinations and standard deviations (in parentheses) are given.
Mean $MA_{buffer}$ ratios: Drug VI: 15393 (2629), Drug VII: 5631 (212), (n = 12);
[b]= Plasma concentrations at equilibrium are related to native plasma under consideration of the dilution factor

TABLE 4

Planning of an experiment for a hypothetical drug with an assumed free fraction of 0.5% and a $MA_{buffer}$ value of 10 000 (for the calculation the lipid content of the batch Transil ® was set to 10.0 μl/ml, the dry weight was set to 269 mg/ml. In the case of buffer volumes are calculated for 10 fold diluted Transil ® ).

| medium | $n_{buffer}/n_{lipid}$ accepted | $V_{total}$ [ml] | $V_{Transil}$ [μl] incubation [1] | $V_{Transil}$ [μl] incubation [2] | $MA_{buffer}$ range | Dilution of Plasma incubation [1] | Dilution of Plasma incubation [2] | $f_u$ diluted Plasma [%] range | $f_u$ undiluted Plasma [%] range |
|---|---|---|---|---|---|---|---|---|---|
| buffer | 2.3 | 0.5 | 25.0 | 125 | 865->100000 | — | — | — | — |
| plasma | 2.3 | 0.5 | 54.0 | 54.0 | — | 1:20 | 1:100 | 3.98-51.3 | 0.041-5.0 |

TABLE 5

Equilibrium drug concentration in native plasma in dependence of $f_u$, $MA_{buffer}$ and the dilution factor of plasma (Lipid content: 72.0 μl/ml, dry weight Transil ®: 223 mg/ml, MW drug: 459).

| | Drug A | | Drug B | |
|---|---|---|---|---|
| $f_u$ [%] | 0.500 | | 0.100 | |
| $MA_{buffer}$ | 10000 | | 50000 | |
| dilution factor of plasma | 1.00 | 0.010 | 1.00 | 0.010 |
| $C_{total}$, maximal [μg/ml] | 232 | 3.61 | 232 | 2.65 |
| $C_{plasma}$, native [μM] | 263 | 393 | 263 | 289 |
| Lipid cont/$n_{lipid}$ [Mol/Mol] | 100 | 100 | 100 | 100 |

TABLE 6

Maximum incubation concentration of a drug in dependence of $MA_{buffer}$ and $n_{buffer}/n_{lipid}$ (Lipid content: 72.0 μl/ml, dry weight Transil ®: 223 mg/ml, MW drug: 459, incubation volume: 0.5 ml).

| | $n_{buffer}/n_{lipid}$ accepted | | | | | |
|---|---|---|---|---|---|---|
| | 1.0 | | 0.10 | | 0.05 | |
| $MA_{buffer}$ | 10000 | 100000 | 10000 | 100000 | 10000 | 100000 |
| $V_{transil}$ [μl] | 0.694 | 0.0694 | 6.93 | 0.694 | 13.8 | 1.39 |
| $C_{total}$, maximal [μg/ml] | 1.21 | 0.121 | 6.63 | 0.664 | 12.6 | 1.27 |
| $C_{buffer}$ [μg/ml] | 0.604 | 0.0604 | 0.604 | 0.0604 | 0.604 | 0.0604 |
| Lipid cont/$n_{lipid}$ [Mol/Mol] | 100 | 100 | 100 | 100 | 100 | 100 |

Abbreviations

| | |
|---|---|
| C | Total drug concentration in a solution of a protein |
| $C_u$ | Unbound drug concentration in a solution of a protein |
| $C_{Prot}$ | Total protein concentration in plasma |
| $f_u$ | Fraction of free (unbound) drug in a solution of a protein |
| $K_d$ | Dissociation constant of the protein drug-complex |
| n | Number of binding sites on the protein |
| $C_x$ | Total drug concentration in a solution of a protein at which an x-fold increase of free fraction is observed |

REFERENCES

The following references are considered to be relevant to the subject matter of the invention and have been referenced from within the text by their number:

1. Oldenburg K. 1995. Current and future trends in high throughput screening for drug discovery. Ann Rep Med Chem 33:301-311.
2. Van de Waterbeemd H, Gifford E. 2003. Admet in silico modelling: towards prediction paradise? Nature Reviews/Drug Discovery 2:192-204.
3. Kariv I, Cao H, Oldenburg K R. 2001. Development of a high throughput equilibrium dialysis method. J Pharm Sci 90:580-587.
4. Lipinski C A, Lombardo F, Dominy B W, Feeney P J. 1997. Experimental and computational approaches to estimate solubility and permeability in drug discovery and development settings. Adv Drug Delivery Rev 23:3-25.
5. Garrett E R, Lambert H J. 1973. Pharmacokinetics of trichloroethanol and metabolites and interconversions among variously referenced pharmacokinetic parameters. J Pharm Sci 62:550-572.
6. Garrett E R, Hunt C A. 1974. Physicochemical properties, solubility, and protein binding of $\Delta^9$-tetrahydrocannabinol. J Pharm Sci 63:1056-1064.
7. Urien S, Riant P, Renouard A, Coulomb B, Rocher I, Tillement J P. 1988. Binding of indapamide to serum proteins and erythrocytes. Biochem Pharmacol 37:2963-2966.
8. Schuhmacher J, Bihner K, Witt-Laido A. 2000. Determination of the free fraction and relative free fraction of drugs strongly bound to plasma proteins. J Pharm Sci 89:1008-1021.
9. Loidl-Stahlhofen A, Eckert A, Hartmann T, Schöttner M. 2001. Solid-supported lipid membranes as a tool for determination of membrane affinity: High-throughput screening of a physicochemical parameter. J Pharm Sci 90:599-606.
10. Loidl-Stahlhofen A, Hartmann T, Schöttner M, Rohring C, Brodowsky H, Schmitt J, Keldenich J. 2001. Multilamellar liposomes and solid-supported lipid membranes (TRANSIL): Screening of lipid-water partitioning toward a high-throughput scale. Pharm Res 18:1782-1788.
11. Schuhmacher J, Zimmer D, Tesche F, Pickard V. 2003. Matrix effects during analysis of plasma samples by electrospray and atmospheric pressure chemical ionization mass spectrometry: practical approaches to their elimination. Rapid Commun Mass Spectrom 17:1950-1957.
12. Steinke W, Yamashita S, Tabei M, Ahr H J, Beckermann B, Domdey-Bette A, Goöller G, Schwarz T, Siefert H M. 1996. Cerivastatin, a new inhibitor of HMG-CoA reductase. Jpn Pharmacol Ther 24 (suppl 9):1217-1237.
13. Van de Waterbeemd H, Smith D A, Jones B C. 2001. Lipophilicity in PK design: methyl, ethyl, futile. J Comput Aid Mol Des 15:273-286.
14. Smith D A, Jones B C, Walker D K. 1996. Design of drugs involving the concepts of drug metabolism and pharmacokinetics. Med Res Rev 16:279-301.
15. Poulin P, Theil F P. 2002. Prediction of pharmacokinetics prior to in vivo studies. Mechanism-based prediction of volume of distribution. J Pharm Sci 91:129-156.
16. Du A Y, Sweeny D J, Antonian L. 2002. Direct measurement of the free fraction ratio for two species comparison of plasma protein binding. Drug Metab Rev ABSTR 133: 67.

The invention claimed is:

1. A method for determining the free fraction of a substance comprising
    (a) incubating the substance with a suspension of particles, having a lipophilic surface in a protein-free aqueous medium, wherein the particles and the medium are erythrocyte-free;
    (b) determining the distribution of the substance between the particles and said protein free medium in step (a);
    (c) incubating the substance with a suspension of particles, having a lipophilic surface in a protein-containing aqueous medium, wherein the particles and the medium are erythrocyte-free;
    (d) determining the distribution of the substance between the particles and said protein-containing aqueous medium in step (c);
    (e) determining the free fraction of the substance from the distributions determined under steps (b) and (d).

2. The method of claim 1, wherein said particles are selected from a group consisting of
    particles having a solid core,
    particles having a solid core comprising a silica bead, and
    solid silica particles coated with egg yolk phosphatidylcholine.

3. The method of claim 1 or 2, wherein the protein-containing aqueous medium is plasma.

4. The method of claim 1 or 2, wherein the protein-free aqueous medium is a buffer solution.

5. The method of claim 1 or 2, wherein said substance is incubated with said suspensions of particles on a plate having multiple cavities or on a 96-well-plate.

6. The method of claim 2, wherein said particles have a ferromagnetic solid core.

7. The method of claim 2, wherein said particles have a solid core and are coated with lipophilic drugs.

8. A method for determining the relative free fraction of a substance in a first species in relation to the free fraction of the same substance in a second species comprising
    (a) determining the membrane affinity of said substance in plasma ($MA_{plasma}$) of said first species,
    (b) determining the membrane affinity of said substance in plasma ($MA_{plasma}$) of said second species,
    (c) determining the relative free fraction from the results determined under the steps (a) and (b);
    provided that the membrane affinity of said substance in plasma ($MA_{plasma}$) of said first species and said second species is determined in an erythrocyte-free environment.

* * * * *